(12) United States Patent
Winfree et al.

(10) Patent No.: US 8,821,526 B2
(45) Date of Patent: Sep. 2, 2014

(54) TROCAR

(75) Inventors: Alan Winfree, Franklin, TN (US); Stan Ashburn, Clarksville, TN (US); Robert Henry, Nashville, TN (US)

(73) Assignee: Specialtycare, Inc., Nashville, TN (US)

( * ) Notice: Subject to any disclaimer, the term of this patent is extended or adjusted under 35 U.S.C. 154(b) by 0 days.

(21) Appl. No.: 13/294,474

(22) Filed: Nov. 11, 2011

(65) Prior Publication Data

US 2012/0123460 A1 May 17, 2012

Related U.S. Application Data

(60) Provisional application No. 61/412,545, filed on Nov. 11, 2010.

(51) Int. Cl.
A61B 17/34 (2006.01)

(52) U.S. Cl.
CPC ....... *A61B 17/3421* (2013.01); *A61B 2017/346* (2013.01)
USPC ........................................................ 606/185

(58) Field of Classification Search
CPC .................... A61B 17/3421; A61B 2017/346
USPC .......................... 606/185, 167; 600/114, 104; 604/164.01, 164.03, 164.08, 164.11, 604/264; D24/146
See application file for complete search history.

(56) References Cited

U.S. PATENT DOCUMENTS

| | | | |
|---|---|---|---|
| 5,242,412 A | 9/1993 | Blake, III | |
| 5,256,149 A | 10/1993 | Banik et al. | |
| 5,334,150 A | 8/1994 | Kaali | |
| 5,364,372 A * | 11/1994 | Danks et al. | 604/264 |
| 5,366,445 A | 11/1994 | Haber et al. | |
| 5,376,076 A | 12/1994 | Kaali | |
| 5,380,291 A | 1/1995 | Kaali | |
| 5,385,572 A | 1/1995 | Nobles et al. | |
| 5,387,196 A | 2/1995 | Green et al. | |
| 5,387,197 A * | 2/1995 | Smith et al. | 604/164.12 |
| 5,441,041 A | 8/1995 | Sauer et al. | |
| 5,449,370 A | 9/1995 | Vaitekunas | |

(Continued)

FOREIGN PATENT DOCUMENTS

| | | |
|---|---|---|
| DE | 10333956 | 2/2005 |
| EP | 0665029 | 1/1995 |
| EP | 1707132 | 10/2006 |
| JP | 7250810 | 10/1995 |

OTHER PUBLICATIONS

English Abstract of DE10333956.
English Abstract of JP7250810.

*Primary Examiner* — Tuan V Nguyen
*Assistant Examiner* — Tin Nguyen
(74) *Attorney, Agent, or Firm* — Preston Smirman; Smirman IP Law, PLLC

(57) ABSTRACT

A trocar is described. The trocar is formed of a biocompatible material, such as but not limited to stainless steel. Accordingly, the trocar is reusable for a relatively large number of surgical procedures assuming conventional sterilization techniques are employed after each surgical procedure. Additionally, the trocar is provided with an angled blade design formed on a distal portion of the trocar shaft. More specifically, the blade design includes a first portion extending substantially co-planar to a proximal portion of the tip portion of the trocar shaft and a second portion extending angularly inwardly towards a distal portion of the tip portion of the trocar shaft.

9 Claims, 9 Drawing Sheets

(56) References Cited

U.S. PATENT DOCUMENTS

| | | |
|---|---|---|
| 5,467,762 A | 11/1995 | Sauer et al. |
| 5,499,625 A | 3/1996 | Frass et al. |
| 5,545,150 A | 8/1996 | Danks et al. |
| 5,569,160 A | 10/1996 | Sauer et al. |
| 5,569,291 A | 10/1996 | Privitera et al. |
| 5,569,292 A | 10/1996 | Scwemberger et al. |
| 5,591,192 A * | 1/1997 | Privitera et al. ............... 606/185 |
| 5,603,702 A | 2/1997 | Smith et al. |
| 5,607,440 A | 3/1997 | Danks et al. |
| 5,620,456 A | 4/1997 | Sauer et al. |
| 5,658,236 A | 8/1997 | Sauer et al. |
| 5,697,913 A | 12/1997 | Sierocuk et al. |
| 5,709,671 A | 1/1998 | Stephens et al. |
| 5,738,628 A | 4/1998 | Sierocuk et al. |
| 5,797,943 A | 8/1998 | Danks et al. |
| 5,817,061 A | 10/1998 | Goodwin et al. |
| 5,860,996 A | 1/1999 | Urban et al. |
| 5,868,714 A | 2/1999 | Danks |
| 5,895,377 A | 4/1999 | Smith et al. |
| 5,904,699 A | 5/1999 | Schwemberger et al. |
| 5,916,232 A | 6/1999 | Hart |
| 5,957,888 A | 9/1999 | Hinchliffe |
| 5,957,947 A | 9/1999 | Wattiez et al. |
| 5,980,493 A | 11/1999 | Smith et al. |
| 5,984,908 A | 11/1999 | Davis et al. |
| 6,017,356 A | 1/2000 | Frederick et al. |
| 6,063,099 A | 5/2000 | Danks et al. |
| 6,228,061 B1 | 5/2001 | Flatland et al. |
| 6,319,266 B1 | 11/2001 | Stellon et al. |
| 6,371,967 B1 | 4/2002 | Long et al. |
| 6,656,198 B2 | 12/2003 | Tsonton et al. |
| 6,666,846 B1 | 12/2003 | Turovskiy et al. |
| 6,685,630 B2 | 2/2004 | Sauer et al. |
| 6,702,787 B2 | 3/2004 | Racenet et al. |
| 6,923,783 B2 | 8/2005 | Pasqualucci |
| 7,025,747 B2 | 4/2006 | Smith |
| D542,918 S | 5/2007 | Albrecht et al. |
| 7,320,694 B2 | 1/2008 | O'Heeron |
| 7,322,933 B2 | 1/2008 | Sauer et al. |
| 7,367,960 B2 | 5/2008 | Stellon et al. |
| 7,470,230 B2 | 12/2008 | Smith et al. |
| 7,559,918 B2 | 7/2009 | Pasqualucci |
| 7,585,288 B2 | 9/2009 | Haberland et al. |
| 7,597,701 B2 | 10/2009 | Hueil et al. |
| 7,637,896 B2 | 12/2009 | Voegele et al. |
| 7,686,823 B2 | 3/2010 | Pingleton et al. |
| 7,722,570 B2 | 5/2010 | Almond et al. |
| 7,758,603 B2 | 7/2010 | Taylor et al. |
| 7,794,644 B2 | 9/2010 | Taylor et al. |
| 7,824,327 B2 | 11/2010 | Smith |
| 7,918,826 B2 | 4/2011 | Armstrong et al. |
| 7,947,058 B2 | 5/2011 | Kahle et al. |
| 7,967,791 B2 | 6/2011 | Franer et al. |
| 2002/0072713 A1 | 6/2002 | Almond et al. |
| 2005/0070850 A1 | 3/2005 | Albrecht |
| 2005/0070947 A1 | 3/2005 | Franer et al. |
| 2005/0149096 A1 | 7/2005 | Hilal et al. |
| 2005/0203559 A1 * | 9/2005 | O'Heeron ............... 606/185 |
| 2006/0173479 A1 | 8/2006 | Smith |
| 2006/0264992 A1 | 11/2006 | Franer et al. |
| 2007/0010842 A1 | 1/2007 | Popov |
| 2007/0088277 A1 | 4/2007 | McGinley et al. |
| 2007/0093851 A1 | 4/2007 | Moran et al. |
| 2007/0185453 A1 | 8/2007 | Michael et al. |
| 2007/0251361 A1 * | 11/2007 | Ogston ............... 83/13 |
| 2007/0260273 A1 | 11/2007 | Cropper et al. |
| 2007/0260275 A1 | 11/2007 | Ahlberg et al. |
| 2008/0051735 A1 | 2/2008 | Measamer et al. |
| 2008/0086074 A1 * | 4/2008 | Taylor et al. ............... 604/26 |
| 2008/0294184 A1 | 11/2008 | Smith |
| 2009/0076323 A1 | 3/2009 | Smith et al. |
| 2009/0093833 A1 | 4/2009 | Smith |
| 2009/0270817 A1 | 10/2009 | Moreno et al. |
| 2009/0281376 A1 | 11/2009 | Acosta et al. |
| 2009/0281386 A1 | 11/2009 | Acosta et al. |
| 2009/0281498 A1 | 11/2009 | Acosta et al. |
| 2009/0281500 A1 | 11/2009 | Acosta et al. |
| 2010/0016664 A1 | 1/2010 | Viola |
| 2010/0022959 A1 | 1/2010 | Moran et al. |
| 2010/0081988 A1 | 4/2010 | Kahle et al. |
| 2010/0137895 A1 | 6/2010 | Smith |

* cited by examiner

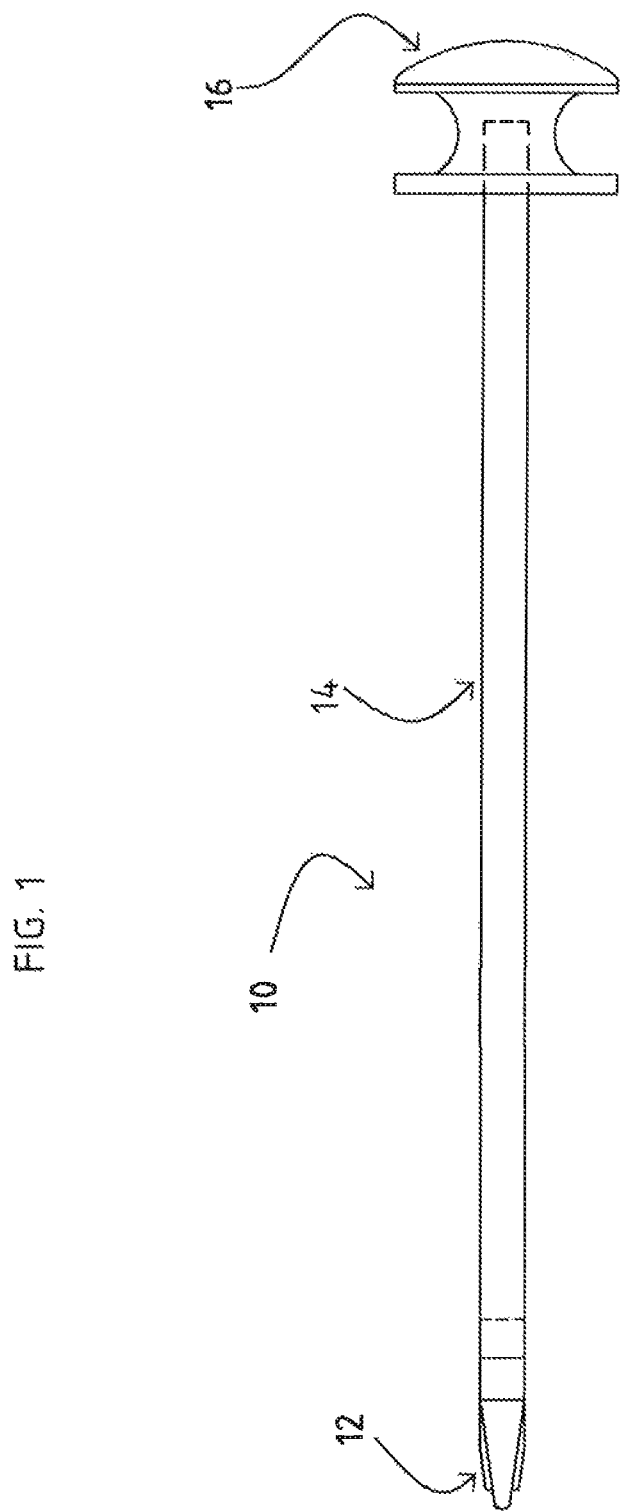

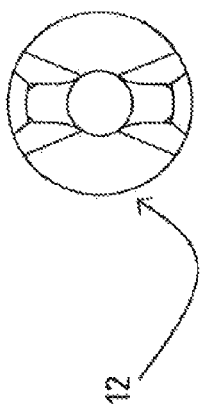
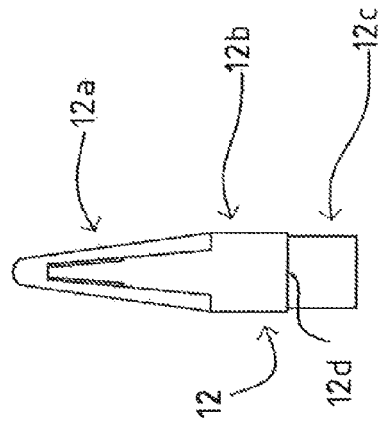
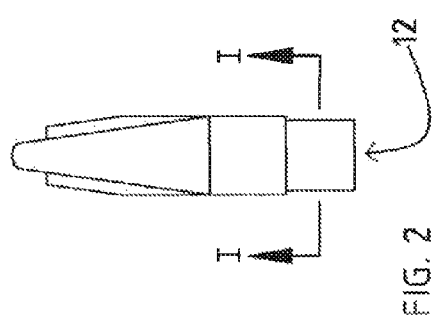
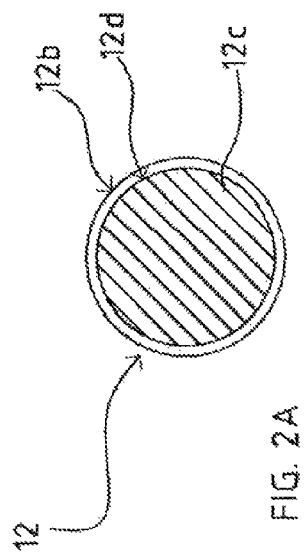

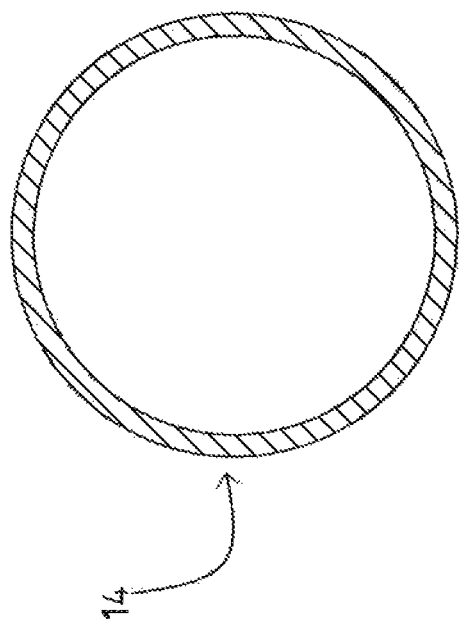
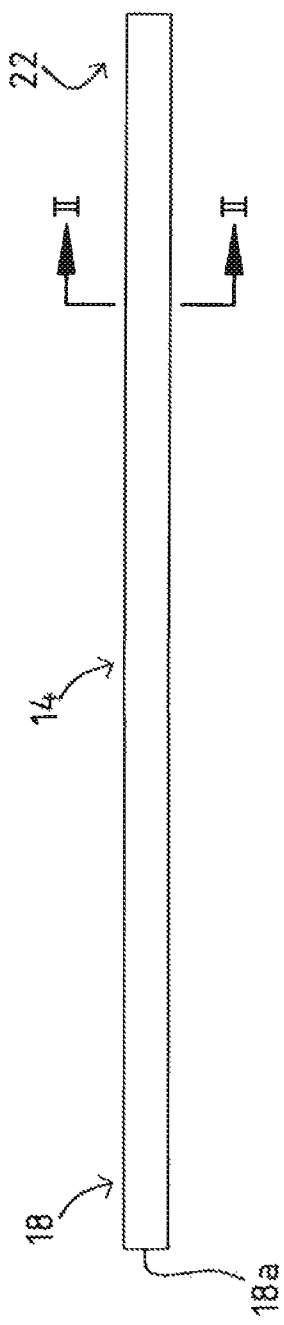
FIG. 3A
FIG. 3

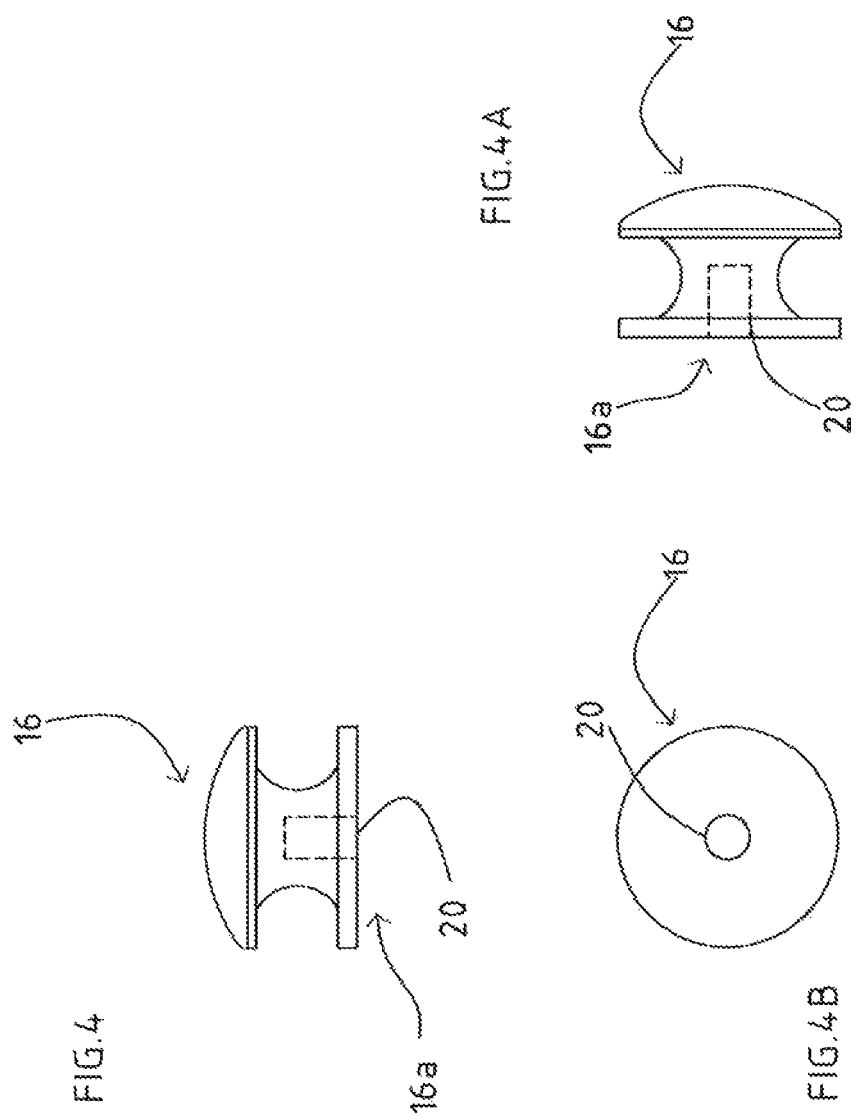

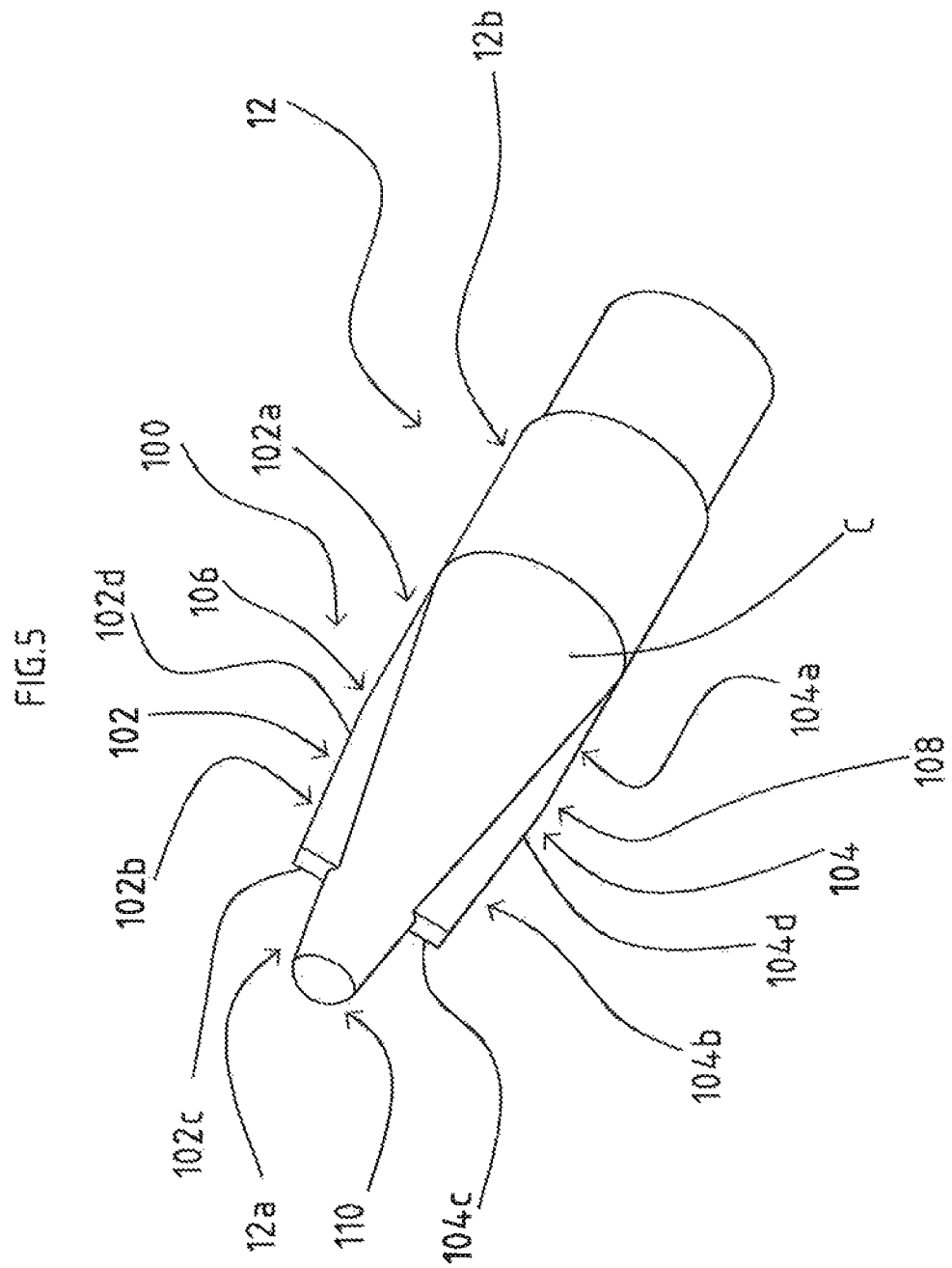

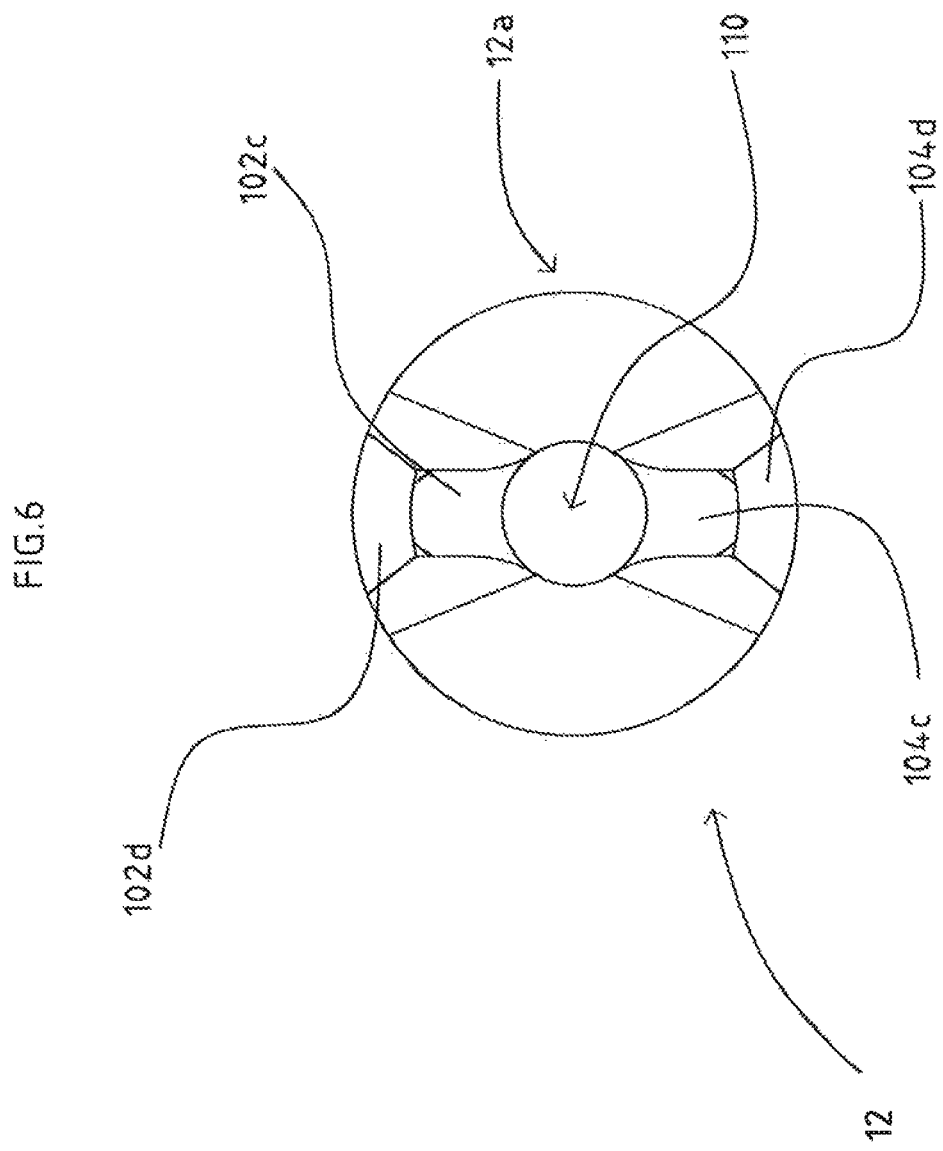

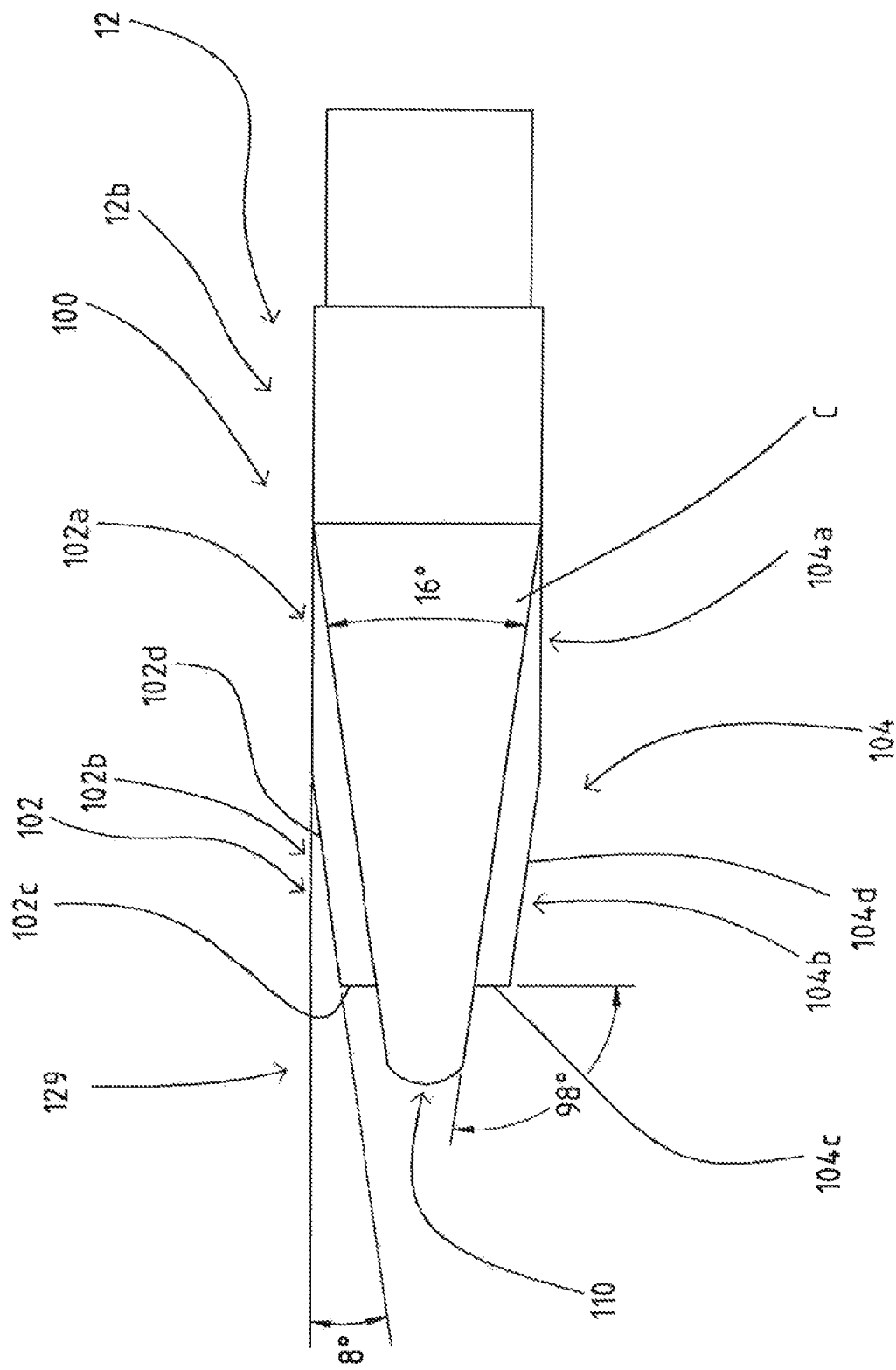

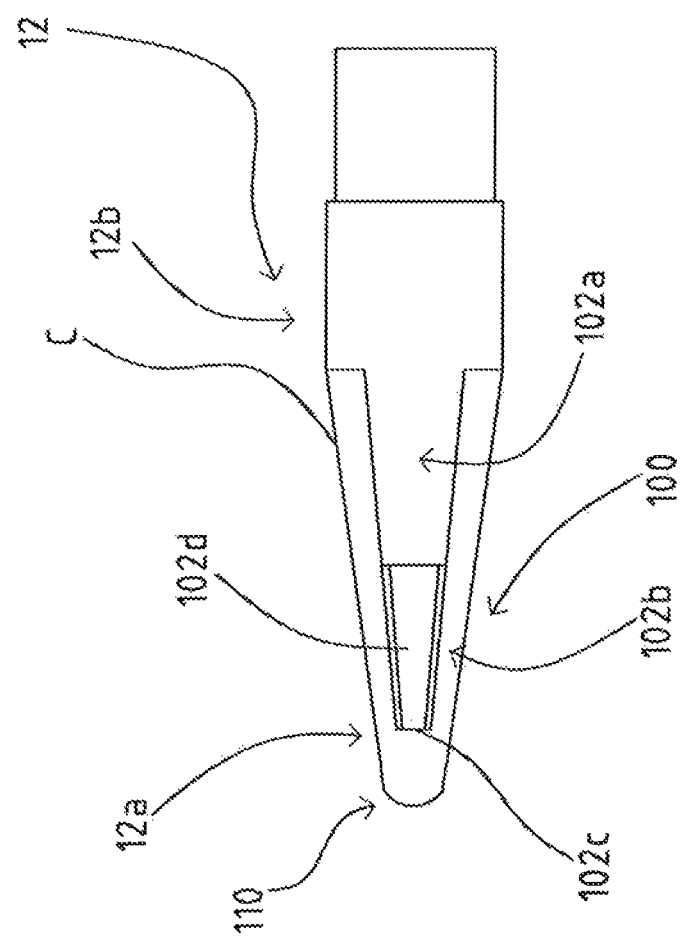

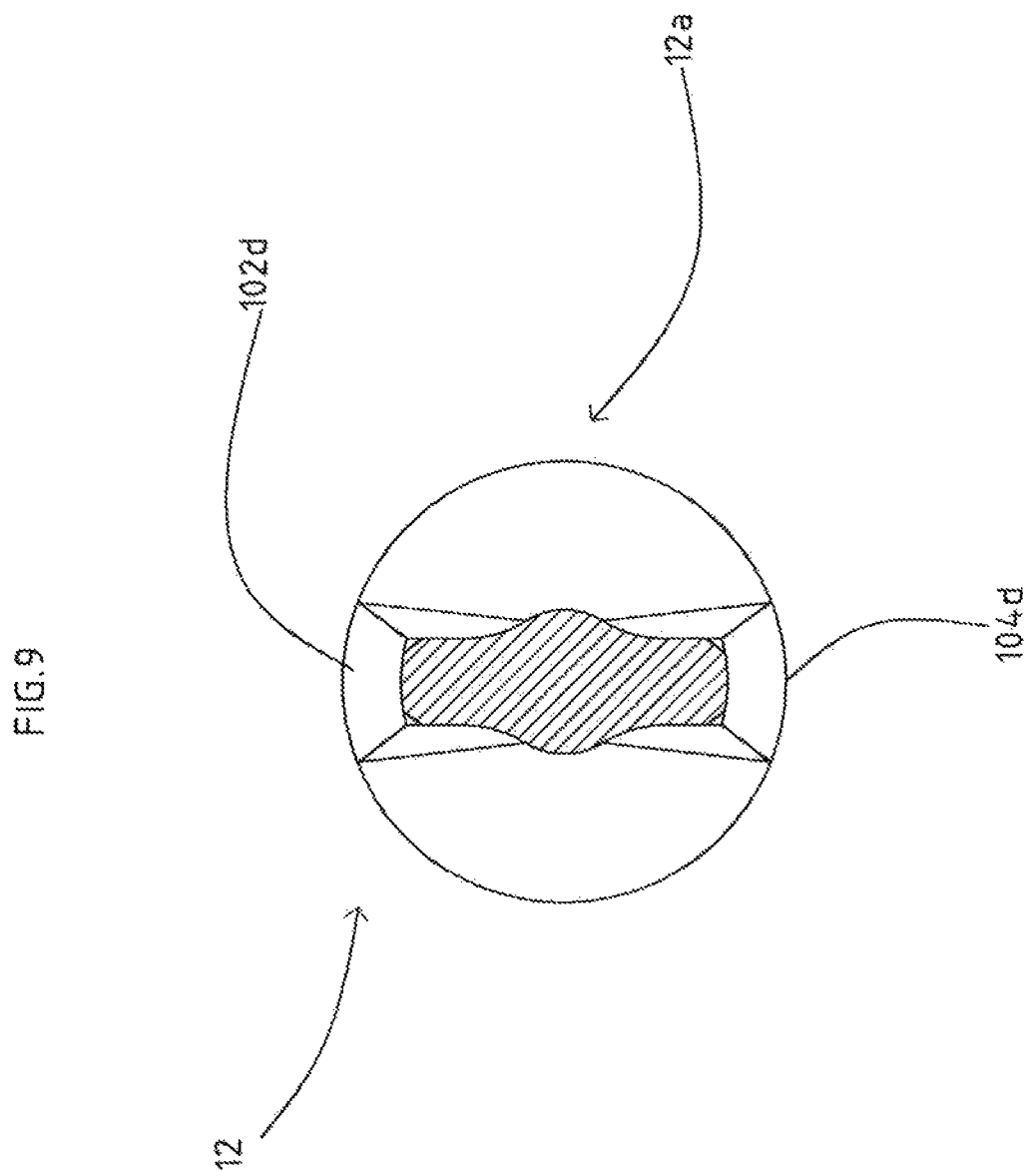

TROCAR

CROSS-REFERENCE TO RELATED APPLICATION

The instant application claims priority to U.S. Provisional Patent Application Ser. No. 61/412,545, filed Nov. 11, 2010, the entire specification of which is expressly incorporated herein by reference.

FIELD OF INVENTION

The present invention relates generally to trocars and more specifically to reusable trocars with an angled blade design formed on, or operably associated with, a tip portion of the trocar shaft, and methods for making the same.

BACKGROUND OF THE INVENTION

Endoscopy, and especially laparoscopic endoscopy, has been a rapidly growing surgical practice in the past decades. Accessing the patient's laparoscopic cavity is typically done via holes, usually punctured with a sharp element referred to as a trocar. In order to penetrate the patient's laparoscopic cavity, the trocar is placed into a tubular element referred to as a cannula, such that the sharp end of the trocar is protruding from the cannula's distal end. The trocar end, when sharp, may puncture the abdominal wall. When a trocar is used, an initial incision to the patient's skin is typically required. Once the cavity has been penetrated by the trocar, it can be withdrawn and various surgical instruments may then be introduced through the cannula and into the cavity.

Surgical trocars are most commonly a single patient use instrument, although there is greater interest in developing reposable (i.e., suitable for a relatively low number of surgical uses) and reusable (i.e., suitable for a relatively high number of surgical uses) trocars that can be appropriately sterilized again and again for use with multiple numbers of patients. Furthermore, modern trocars have graduated from the classical "three point" design that gave them their name, to either a flat bladed "dilating-tip" product, or something that is entirely blade free.

However, there exists a need for new and improved reusable trocars, and methods for making the same, that overcome at least one of the aforementioned disadvantages.

SUMMARY OF THE INVENTION

In accordance with the general teachings of the present invention, a trocar is provided. The trocar allows for penetration into the patient's laparoscopic cavity. The trocar is formed of a biocompatible material, such as but not limited to stainless steel. Accordingly, the trocar is reusable for a relatively large number of surgical procedures assuming conventional sterilization techniques are employed after each surgical procedure. Additionally, the trocar is provided with an angled blade design formed on, or operably associated with, a distal portion of the trocar shaft. More specifically, the blade design includes a first portion extending substantially co-planar to a proximal portion of a tip portion of the trocar shaft and a second portion extending angularly inwardly towards a distal portion of the tip portion of the trocar shaft.

Methods for forming the trocar are also provided.

In accordance with an embodiment of the present invention, a trocar is provided, comprising: a tip portion having a distal portion and a proximal portion; and a blade system formed on a surface of the tip portion, wherein the blade system includes a wing member, wherein the wing member include a first portion and a second portion, wherein the first portion extends in a substantially co-planar orientation relative to the proximal portion of the tip portion, wherein the second portion extends in a substantially angularly inwardly orientation towards the distal portion of the tip portion.

In accordance with an aspect of this embodiment, the proximal portion of the tip portion is substantially cylindrically shaped.

In accordance with an aspect of this embodiment, the distal portion of the tip portion is substantially conically shaped.

In accordance with an aspect of this embodiment, the distal portion of the tip portion includes a taper having an angle in the range of about 12-20°.

In accordance with an aspect of this embodiment, the distal portion of the tip portion includes a taper having an angle in the range of about 14-18°.

In accordance with an aspect of this embodiment, the distal portion of the tip portion includes a taper having an angle of 16°.

In accordance with an aspect of this embodiment, the second portion does not extend to a terminus of the tip portion.

In accordance with an aspect of this embodiment, the first portion and the second portion of the tip portion are angled with respect to one another in the range of about 6-10°.

In accordance with an aspect of this embodiment, the first portion and the second portion of the tip portion are angled with respect to one another in the range of about 7-9°.

In accordance with an aspect of this embodiment, the first portion and the second portion of the tip portion are angled with respect to one another at 8°.

In accordance with an aspect of this embodiment, the second portion includes an area defining a cutting edge formed thereon.

In accordance with an aspect of this embodiment, the cutting edge and the distal portion of the tip portion are angled with respect to one another in the range of about 94-102°.

In accordance with an aspect of this embodiment, the cutting edge and the distal portion of the tip portion are angled with respect to one another in the range of about 96-100°.

In accordance with an aspect of this embodiment, the cutting edge and the distal portion of the tip portion are angled with respect to one another at 98°.

In accordance with an aspect of this embodiment, the second portion includes an area defining a blade edge formed thereon.

In accordance with an aspect of this embodiment, the tip portion is comprised of a biocompatible material.

In accordance with an aspect of this embodiment, a shaft member is provided, wherein the proximal portion of the tip portion is selectively operable to be at least partially received within an area defining a bore formed in a distal portion of the shaft member.

In accordance with an aspect of this embodiment, a handle member is provided, wherein a distal portion of the shaft member is selectively operable to be at least partially received within an area defining a bore formed in a distal portion of the handle member.

In accordance with an aspect of this embodiment, a substantially cylindrically shaped shaft member is provided, wherein the shaft member includes a through bore formed therein, wherein the proximal portion of the tip portion is selectively operable to be at least partially received within the through bore at a distal portion of the shaft member.

In accordance with an aspect of this embodiment, a handle member is provided, wherein a distal portion of the shaft member is selectively operable to be at least partially received within an area defining a bore formed in a distal portion of the handle member.

Further areas of applicability of the present invention will become apparent from the detailed description provided hereinafter. It should be understood that the detailed description and specific examples, while indicating the preferred embodiment of the invention, are intended for purposed of illustration only and are not intended to limit the scope of the invention.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 illustrates an elevational view of a trocar, in accordance with a first embodiment of the present invention;

FIG. 2 illustrates a first side view of a tip portion of a trocar, in accordance with a second embodiment of the present invention;

FIG. 2A illustrates a sectional view taken along line I-I of FIG. 2, in accordance with a third embodiment of the present invention;

FIG. 2B illustrates a second side view of a tip portion of a trocar, in accordance with a fourth embodiment of the present invention;

FIG. 2C illustrates a top plan view of a tip portion of a trocar, in accordance with a fifth embodiment of the present invention;

FIG. 3 illustrates an elevational view of a shaft portion of a trocar, in accordance with a sixth embodiment of the present invention;

FIG. 3A illustrates a sectional view taken along line II-II of FIG. 3, in accordance with a seventh embodiment of the present invention;

FIG. 4 illustrates an elevational view of a handle portion of a trocar, in accordance with an eighth embodiment of the present invention;

FIG. 4A illustrates a side view of a handle portion of a trocar, in accordance with a ninth embodiment of the present invention;

FIG. 4B illustrates a bottom plan view of a handle portion of a trocar, in accordance with a tenth embodiment of the present invention;

FIG. 5 illustrates a perspective view of a tip portion of a trocar, in accordance with an eleventh embodiment of the present invention;

FIG. 6 illustrates a top plan view of a tip portion of a trocar, in accordance with a twelfth embodiment of the present invention;

FIG. 7 illustrates an elevational view of a tip portion of a trocar, in accordance with a thirteenth embodiment of the present invention;

FIG. 8 illustrates a side view of a tip portion of a trocar, in accordance with a fourteenth embodiment of the present invention; and FIG. 9 illustrates a top plan view of a tip portion (with a portion thereof shown in section) of a trocar, in accordance with a fifteenth embodiment of the present invention.

The same reference numerals refer to the same parts throughout the various Figures.

DETAILED DESCRIPTION OF THE INVENTION

The following description of the preferred embodiment(s) is merely exemplary in nature and is in no way intended to limit the invention, or uses.

Referring to FIG. 1, there is shown a trocar generally at 10. The trocar 10 primarily includes, without limitation, a tip portion 12, a shaft portion 14, and a handle portion 16. It should be appreciated that the trocar 10 of the present invention may be operable to interoperate with a cannula or similar device during a surgical procedure.

Referring to FIGS. 2-2C, there are shown several views of the tip portion 12. The tip portion 12 is shown as having a substantially cone-shaped distal portion 12a, a substantially cylindrically-shaped intermediate (also referred to as an intermediate proximal portion) portion 12b, and a substantially cylindrically-shaped proximal portion 12c. In accordance with one aspect of this embodiment, the proximal portion 12c may be provided with a smaller diameter than the intermediate portion 12b so as to form an annular shoulder portion 12d, the intended purpose of which will be described herein. Although one or more portions of the tip portion 12 are shown as being solid, it should be appreciated that one or more portions of the tip portion 12 may be at least partially hollow. The tip portion 12 may be comprised of a biocompatible material, such as but not limited to stainless steel.

Referring to FIGS. 3-3A, there are shown several views of the shaft portion 14. In this view, the shaft portion is shown as being substantially cylindrical. Although one or more portions of the shaft portion 14 are shown as being hollow, it should be appreciated that one or more portions of the shaft portion 14 may be at least partially solid. The shaft portion 14 may be preferably comprised of a biocompatible material, such as but not limited to stainless steel. By way of a non-limiting example, the proximal portion 12c of the tip portion 12 may be received within and/or joined to a distal end portion 18 of shaft portion 14 by any number of methods including, but not limited to brazing and/or the like. By way of a non-limiting example, the shoulder portion 12d of the tip portion 12 may abut against the end surface 18a of the distal end portion 18 and act as a stop. Alternatively, the tip portion 12 and the shaft portion 14 may be formed integrally together from a single piece of material.

Referring to FIGS. 4-4B, there are shown several views of the handle portion 16. The handle portion 16 is preferably comprised of a biocompatible material, such as but not limited to stainless steel. By way of a non-limiting example, a proximal portion 22 of the shaft portion 14 may be joined to the distal portion 16a of the handle portion 16 by any number of methods including, but not limited to welding and/or the like. For example, a recess 20 may be formed in the distal portion 16a of the handle portion 16, wherein the proximal portion 22 of the shaft portion 14 may be received therein. Alternatively, the shaft portion 14 and the handle portion 16 may be formed integrally together from a single piece of material.

Referring to FIGS. 5-9, there is shown a tip portion 12 that includes a blade system 100 formed thereon. The blade system 100 may include two spaced and opposed wing members 102, 104, respectively. The wing members 102, 104, respectively, may be formed on the tip portion 12 by any number of methods, including but not limited to grinding and/or the like.

Each of the wing members 102, 104, respectively, may include a first portion 102a, 104a, respectively, and a second portion 102b, 104b, respectively.

The first portions 102a, 104a, respectively, may extend in a substantially co-planar orientation relative to the intermediate portion 12b of the tip portion 12. The second portions 102b, 104b, respectively, may extend in a substantially angularly inwardly orientation towards the distal portion 12a of the tip portion 12. The second portions 102b, 104b, respectively, at about points 106, 108, respectively, may begin to extend in a substantially angularly inwardly orientation towards the distal portion 12a of the tip portion 12.

The cone portion C of the tip portion 12 may taper inwardly towards the distal portion 12a at an angle in the range of about 12-20°, more preferably in the range of about 14-18°, and an angle of about 16° being most preferred. The second portions 102b, 104b, respectively, do not have to extend all the way to the terminus 110 of the tip portion 12; but rather, they may terminate at a location prior to or short of the terminus 110. The exact angle formed between the first portions 102a, 104a, respectively, and the second portions 102b, 104b, respectively, is not thought to be critical to the operation of the present invention; however, an angle in the range of about 6-10° is preferred, an angle in the range of about 7-9° being more preferred, and an angle of about 8° being most preferred.

The second portions 102b, 104b, respectively, may include areas defining a cutting edge 102c, 104c, respectively, and a blade edge 102d, 104d, respectively, that are selectively operable to cut through various bodily tissues so as to penetrate a patient's bodily cavities. That is, cutting edges 102c, 104c, respectively, and blade edges 102d, 104d, respectively, may be formed with areas of sufficient sharpness so as to penetrate and cut through tissue without undue effort by the surgeon. The angle formed by cutting edge 102c and distal portion 108 may be preferably in the range of about 94-102°, more preferably in the range of about 96-100°, and most preferably 98° Likewise, the angle formed by cutting edge 104c and distal portion 108 may be preferably in the range of about 94-102°, more preferably in the range of about 96-100°, and most preferably 98°.

Because the trocar 10 of the present invention is comprised of materials that can be sterilized many times without any degradation of the materials, the trocar 10, including its component parts thereof, is reposable and/or reusable and can thus be used for a relatively large number of surgical procedures, assuming conventional sterilization techniques are employed after each surgical procedure.

While the invention has been described with reference to an exemplary embodiment, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A trocar, comprising:
a tip portion having a distal portion, a proximal portion and a body defining a longitudinal axis extending from the distal portion to the proximal portion, wherein the proximal portion of the tip portion is substantially cylindrically shaped, wherein the distal portion of the tip portion is substantially conically shaped, wherein the distal portion of the tip portion includes a taper having an angle of 16° from the longitudinal axis of the body, wherein the taper angle is defined by the angle between two straight edges located 180° about the longitudinal axis; and
a blade system formed on a surface of the tip portion, wherein the blade system includes a wing member, wherein the wing member includes a first portion and a second portion, wherein the first portion is co-planar to the proximal portion of the tip portion, wherein the second portion extends in a substantially angularly inwardly orientation towards the distal portion of the tip portion;
wherein the first portion and the second portion of the wing member are angled with respect to one another, wherein the angle is 8°;
wherein the second portion includes a first area defining a first cutting edge formed thereon;
wherein the second portion includes a second area defining a second cutting edge formed thereon;
wherein the second cutting edge and the distal portion of the tip portion are angled with respect to one another at 98°.

2. The trocar according to claim 1, wherein the second portion does not extend to a terminus of the tip portion.

3. The trocar according to claim 1, wherein the tip portion is comprised of a biocompatible material.

4. The trocar according to claim 1, further comprising a shaft member, wherein the proximal portion of the tip portion is selectively operable to be at least partially received within an area defining a bore formed in a distal portion of the shaft member.

5. The trocar according to claim 4, further comprising a handle member, wherein a proximal portion of the shaft member is selectively operable to be at least partially received within an area defining a bore formed in a distal portion of the handle member.

6. The trocar according to claim 1, further comprising a substantially cylindrically shaped shaft member, wherein the shaft member includes a through bore formed therein, wherein the proximal portion of the tip portion is selectively operable to be at least partially received within the through bore at a distal portion of the shaft member.

7. The trocar according to claim 6, further comprising a handle member, wherein a proximal portion of the shaft member is selectively operable to be at least partially received within an area defining a bore formed in a distal portion of the handle member.

8. A trocar, consisting of:
a tip portion having a distal portion, a proximal portion and a body defining a longitudinal axis extending from the distal portion to the proximal portion, wherein the proximal portion of the tip portion is substantially cylindrically shaped, wherein the distal portion of the tip portion is substantially conically shaped, wherein the distal portion of the tip portion includes a taper having an angle of 16° from the longitudinal axis of the body, wherein the taper angle is defined by the angle between two straight edges located 180° about the longitudinal axis; and
a blade system formed on a surface of the tip portion, wherein the blade system includes a wing member, wherein the wing member includes a first portion and a second portion, wherein the first portion is co-planar to the proximal portion of the tip portion, wherein the second portion extends in a substantially angularly inwardly orientation towards the distal portion of the tip portion;
wherein the first portion and the second portion of the wing member are angled with respect to one another, wherein the angle is 8°;
wherein the second portion includes a first area defining a first cutting edge formed thereon;
wherein the second portion includes a second area defining a second cutting edge formed thereon;
wherein the second cutting edge and the distal portion of the tip portion are angled with respect to one another at 98°.

9. A trocar, comprising:

a tip portion having a distal portion, a proximal portion and a body defining a longitudinal axis extending from the distal portion to the proximal portion, wherein the proximal portion of the tip portion is substantially cylindrically shaped, wherein the distal portion of the tip portion is substantially conically shaped, wherein the distal portion of the tip portion includes a taper having an angle in the range of 12° to 20° from the longitudinal axis of the body, wherein the taper angle is defined by the angle between two straight edges located 180° about the longitudinal axis; and a blade system formed on a surface of the tip portion, wherein the blade system includes a wing member, wherein the wing member includes a first portion and a second portion, wherein the first portion is co-planar to the proximal portion of the tip portion, wherein the second portion extends in a substantially angularly inwardly orientation towards the distal portion of the tip portion, wherein the second portion includes a center wall portion and a pair of spaced and opposed sidewall portions;

wherein the first portion and the second portion of the wing member are angled with respect to one another, wherein the angle is in the range of about 6° to 10°;

wherein the second portion includes a first area defining a first cutting edge formed thereon;

wherein the second portion includes a second area defining a second cutting edge formed thereon;

wherein the second cutting edge and the distal portion of the tip portion are angled with respect to one another in the range of about 94° to 102°.

\* \* \* \* \*